United States Patent [19]
Ooi et al.

[11] Patent Number: 6,072,092
[45] Date of Patent: Jun. 6, 2000

[54] RECOVERY OF CAROTENES

[75] Inventors: Cheng Keat Ooi; Yuen May Choo; Ah Ngan Ma; Soon Chee Yap, all of Selangor Darul Ehsan, Malaysia

[73] Assignee: Palm Oil Research & Development Board, Selangor, Malaysia

[21] Appl. No.: 08/640,398

[22] Filed: Apr. 30, 1996

Related U.S. Application Data

[63] Continuation of application No. 08/304,597, Sep. 12, 1994, abandoned.

[30] Foreign Application Priority Data

Mar. 18, 1994 [MY] Malaysia ............................ PI 9400659

[51] Int. Cl.⁷ .................................................. C07C 403/00
[52] U.S. Cl. ............................................ 585/351; 585/864
[58] Field of Search ...................... 585/351, 864

[56] References Cited

U.S. PATENT DOCUMENTS 5,019,668  5/1991  Keat et al. .............................. 585/864
5,157,132  10/1992  Tan et al. ................................ 585/413

FOREIGN PATENT DOCUMENTS 2160874  10/1987  United Kingdom.
2218989  4/1991  United Kingdom.

*Primary Examiner*—John F. Niebling
*Assistant Examiner*—Alexander G. Ghyka
*Attorney, Agent, or Firm*—Ladas & Parry

[57] ABSTRACT

A process for the recovery of carotenes and the production of carotene concentrate from natural oils and fats. The carotene-containing natural oils and fats is subjected to alcoholic esterification to form a mixture of fatty acid alkyl esters, carotenes, tocopherols and tocotrienols. The alkyl esters mixture is subjected to vacuum distillation at a pressure of less than 60 mTorr and a temperature of less than 180° C. to form a carotene-rich concentrate. The carotenes in the carotene-rich concentrate are adsorptively separated, concentrated and collected as carotene-rich fraction.

4 Claims, No Drawings

RECOVERY OF CAROTENES

This application is a continuation of application Ser. No. 08/304,597 filed on Sep. 12, 1994 now abandoned.

BACKGROUND OF THE INVENTION

This invention relates to the process of producing carotene concentrates from carotene-containing natural oils and fats and has particular but not exclusive application to the process of producing carotene concentrate from palm oil.

Carotenes are natural color pigments found in plants and animals. These are widely used for applications in food, pharmaceutical and nutritional products. Some carotenes are known to have provitamin A activity, in particular beta-carotene. The carotenes are also shown to inhibit tumour growth and associated with the prevention of cancer formation such as oral, pharyngeal, lung and stomach cancer.

The major sources of natural carotenes are from vegetables, fruits and vegetable oil such as palm oil. Among these sources, palm oil is the richest source of natural carotenes. The orange red color of palm oil is due to the presence these carotenes. The carotene concentration of palm oil can range from 500 ppm to 3000 ppm, depending on the species of the palm from which the oil is extracted. The major carotenes present in palm oil are alpha- and beta-carotene. These two carotenes make up about 90% of the carotenes in palm oil.

A number of patents have been filed on the recovery of carotenes from palm oil and they are U.S. Pat. No. 5,157,132, UK Patents GB 2160874A and GB 2218989. The processes filed under these patents also employed adsorbent in some stage of the recovery process. In the U.S. Pat. No. 5,157,132 alumina was used, while resin and reverse phase C18 silica gel were used in GB 21 60874A and GB 2218989 patent respectively. This invention relates specifically to the use of normal silica gel to recover natural carotenes from natural oils and fats. At present the commercial production of natural carotenes comes mainly from carrot and algae, and small amount from palm oil. However, the present process for the recovery of carotenes from natural oils and fats are expensive and involves many steps.

Therefore, a need exists for a simple and inexpensive method for extracting carotenes from natural oils and fats.

SUMMARY OF THE INVENTION

The present invention relates to a process for the recovery of carotenes from carotene-containing natural oils and fats, and the production of carotene concentrate from palm oil, which comprises the steps of alcoholic esterification of palm oil, collecting the oil phase containing carotenes, tocopherols, tocotrienols, sterols and fatty acid alkyl esters, followed by vacuum distillation of the mixture at a pressure of less than 60 mTorr and a temperature of less than 180° C., to give a carotene-rich concentrate and selectively separates carotenes from the carotene-rich concentrate to give carotene-rich fraction. This invention involves an additional step and is an improvement over the previous U.S. Pat. No. 5,019,668.

This invention has many advantages. It involves only a few simple steps. The separation of the carotenes from the carotene-rich concentrate is carried out through a short column and the eluting solvent are food grade materials.

DETAILED DESCRIPTION OF THE INVENTION

Palm oil consists of mainly the triglycerides, also contains minor components like carotenes, tocopherols and tocotrienols. The edible oil is esterified with alcohols such as methanol, ethanol or isopropanol to give a mixture of glycerol, alkyl esters of fatty acids, carotenes, tocopherols and tocotrienols. Carotenes in the oils and fats are contained along with the unreacted glycerides in the alkyl ester phase (oil phase). The oil phase is separated from glycerin by standing or centrifuging. The oil phase collected is a mixture of alkyl esters, tocopherols, tocotrienols and carotenes. The carotene-containing natural oils and fats used is preferably palm oil and its products, such as palm olein, palm stearin, neutralized palm oil or neutralized palm olein.

In the subsequent step, the oil phase containing carotenes, tocopherols and tocotrienols is subjected to a distillation process to remove the alkyl esters, leaving a concentrate rich in carotenes, tocopherols and tocotrienols. The carotenes in the concentrate are substantially stable over a long period of time and have a concentration of more than 3,000 ppm and above. The carotene concentration can range from 3,000 ppm to 40,000 ppm. This can be higher, depending on the carotene concentration of the starting material. Preferably, in the distillation process, the alkyl esters mixture is heated to a required temperature of not more than 180° C. and a pressure of not more than 60 mTorr. The distilled alkyl esters and the carotene concentrate are collected in separate containers.

The carotene-rich concentrate collected as mentioned above is brought into contact with a non-polar solvent and then with silica-gel adsorbent, whereby carotenes, tocopherols and tocotrienols and other residual glycerides are adsorbed on the adsorbent. Subsequently, the adsorbent is brought into contact with a non-polar solvent, such as hexane, heptane or petroleum ether, so that carotenes are separated from other components of the carotene-rich concentrate and the solution containing carotene in high concentration is obtained. The carotenes are easily separated from the other components of the carotene-rich concentrate because they adsorb less strongly on the adsorbent than the other components of the concentrate. After the separation of the carotenes, the adsorbent is brought into contact with a polar solvent or a mixture of polar solvents such as methanol, ethanol, isopropanol or chloroform. This removes the other components such as tocopherols, tocotrienols, sterols and glycerides from the adsorbent and the solution containing tocopherols, tocotrienols, sterols in high concentration is obtained.

There are no specific limitations in the method of bringing the carotene-rich concentrate to the adsorbent. Contact may be accompanied by using a column or batchwise. The preferred method is by using column because of the efficient separation of the carotenes. The contacting of the carotene-rich concentrate with the adsorbent can be performed more efficiently if the concentrate is previously diluted with a non-polar solvent which is used for the elution of carotenes in the subsequent step. For the elution of carotenes, the non-polar solvent can be used in an amount of 5 to 20 times the weight of the adsorbent or higher. There are no specific restrictions in the type of non-polar solvent used in eluting carotenes. Preferred examples are hexane, heptane and petroleum ether. They may be used individually or in combination with another. Hexane is particularly preferable from the standpoint of safety in the case where the recovered carotenes are used for food. e.g. as edible coloring. The solvent in the carotenes which have been separated from the adsorbent is distilled away in the usual way. The carotene content in the carotene-rich fraction ranged from 30% to 100%. Various ranges of carotene concentrate from 1% to 30% can then be prepared by blending or mixing edible oil or solution with the carotene-rich fraction before or after the removal of the non-polar solvent.

After the separation of the carotenes, the adsorbent is brought into contact with a polar solvent, where the other components of the concentrate such as tocopherols, tocotrienols, sterols are eluted from the column. There is no specific limitation in the type of polar solvent used in eluting. Preferred solvents are methanol, ethanol and isopropanol. These alcohols may be used individually or in combination with one another or in combination with non-polar solvent. For the elution of the other components of the concentrate, the polar solvent may be used in an amount of 3 to 10 times the weight of the adsorbent or higher. The solvent in the other components which have been eluted from the adsorbent is distilled away in the usual way.

As mentioned above, the process of the invention comprises the step of subjecting carotene-containing natural oils and fats to alcoholic esterification, collecting the oil phase containing carotenes, tocopherols, tocotrienols, sterols and alkyl esters, distilling away the alkyl esters and collecting carotene-rich concentrate, and selectively separates carotene-rich fraction form the other components of the carotene-rich concentrate. The process of this invention does not include high temperature step and hence recovers carotenes in high yield without loss due to decomposition. In addition, it affords as a by-product fatty acid alkyl esters with carotene removed and a concentrate rich in tocopherols, tocotrienols and sterols.

In a preferred embodiment of the process, the carotene-rich concentrate is mixed with a non-polar solvent and contacting with silica-gel, followed by separating the carotenes from the other components of the concentrate with a non-polar solvent and distilling away the solvent to give carotene-rich fraction.

The present invention will now be further and specifically described by the following examples. All parts and percentages are by weight unless otherwise stated.

EXAMPLE I

Crude palm oil methyl esters and carotene, derived from the alcoholic esterification of crude palm oil with 1 to 2% base catalyst and methanol was passed through molecular distillation, at a temperature of 130–170° C., and pressure of less than 60 mTorr to give a 4% carotene concentrate.

An open column having a length of one hundred millimeters and an internal diameter of thirty millimeters was wet packed with hexane and silica gel (10 gram, 70–230 mesh grade), commercially available from Merck. A 0.25 gram sample of the 4% carotene concentrate was dissloved in 5 milliliters of hexane was added to the top of the column. An eluant hexane was then added to the column by gravity to separate carotenes from the concentrate. Four hundred milliliters of hexane eluate was collected from the bottom of the column and rotavaporized to give a carotene-rich fraction. A 50% mixture of isopropanol and hexane was then added to the column to eluate the remaining components of the concentrate from the column. Two hundred milliliters of the admixture was collected and rotavaporized. The carotene concentration of the rotavaporized sample was then measured by spectrophotometery using Hitachi U-2000 spectrophotometer. The concentration of carotene of the first fraction (carotene-rich fraction) and the second fraction as determined by spectrophotometry was about 340,000 ppm and 6,500 ppm respectively.

EXAMPLE II

An open column having a length of one hundred millimeters and an internal diameter of thirty millimeters was wet packed with hexane and silica gel (10 gram, 70–230 mesh grade), commercially available from Merck. A 0.50 gram sample of the 4% carotene concentrate obtained in the same manner as in Example I was dissloved in 5 milliliters of hexane was introduced to the packing at the top of the column. Carotenes, as indicated by the orange band was eluated from the column by gravity with hexane. Two hundred milliliters of hexane eluate was collected from the bottom of the column and rotavaporized to give a carotene-rich fraction. A 50% mixture of ethanol and hexane was then added to the column to eluate the remaining components of the concentrate from the column. One hundred milliliters of the admixture was collected and rotavaporized. The carotene concentration of the rotavaporized sample was then measured by spectrophotometery using Hitachi U-2000 spectrophotometer. The concentration of carotene of the first fraction (carotene-rich fraction) and the second fraction as determined by spectrophotometry was about 520,000 ppm and 6,900 ppm respectively. In addition the vitamin E content of the second fraction was determined and analyzed by HPLC on Lichrosob 5 Silica 60A column, having a dimension of 25 cm×0.46 cm with fluorescence detector. The mobile phase in the column was 96% hexane, 3.8% tetrahydrofuran and 0.2% isopropanol. The vitamin E content of the second fraction as determined by HPLC was about 6,700 ppm. Yield of carotenes recovery was about 99%.

EXAMPLE III

An open column having a length of one hundred millimeters and an internal diameter of thirty millimeters was wet packed with hexane and silica gel (10 gram, 70–230 mesh grade), commercially available from Merck. A 0.50 gram sample of the 4% carotene concentrate obtained in the same manner as in Example I was dissloved in 5 milliliters of hexane was introduced to the packing at the top of the column. Carotenes, as indicated by the orange band was eluated from the column by gravity with hexane. Two hundred milliliters of hexane eluate was collected from the bottom of the column and rotavaporized to give a carotene-rich fraction. A 50% mixture of methanol and hexane was then added to the column to eluate the remaining components of the concentrate from the column. One hundred milliliters of the admixture was collected and rotavaporized. The concentration of carotene of the first fraction (carotene-rich fraction) and the second fraction as determined by spectrophotometry in Example I and II was about 332,000 ppm and 6,700 ppm respectively. In addition the vitamin E content of the second fraction was determined and analyzed by HPLC on Lichrosob 5 Silica 60A column, having a dimension of 25 cm×0.46 cm with fluorescence detector. The mobile phase in the column was 96% hexane, 3.8% tetrahydrofuran and 0.2% isopropanol. The vitamin E content of the second fraction as determined by HPLC was about 5,300 ppm. Yield of carotenes recovery was about 99%.

EXAMPLE IV

An open column having a length of one hundred millimeters and an internal diameter of thirty millimeters was wet packed with hexane and silica gel (10 gram, 70–230 mesh grade), as in Example II and Ill. A 0.50 gram sample of the 4% carotene concentrate obtained in the same manner as in Example I was dissloved in 5 milliliters of hexane was introduced to the packing at the top of the column. Carotenes, as indicated by the orange band was eluated from the column by gravity with hexane. Two hundred milliliters of hexane eluate was collected from the bottom of the column and rotavaporized to give a carotene-rich fraction. Isopropanol was then added to the column to eluate the remaining components of the concentrate from the column. One hundred milliliters of the eluate was collected and rotavaporized. The concentration of carotene of the first fraction (carotene-rich fraction) and the second fraction as determined by spectrophotometry in Example I and II was about 410,000 ppm and 7,000 ppm respectively. The vitamin E content of the second fraction as determined by HPLC in Example II and III was about 5,800 ppm. Yield of carotenes recovery was about 99%.

EXAMPLE V

An open column having a length of one hundred millimeters and an internal diameter of thirty millimeters was wet packed with hexane and silica gel (10 gram, 70–230 mesh grade), as in Example II and III. A 0.50 gram sample of the 4% carotene concentrate obtained in the same manner as in Example I was dissloved in 5 milliliters of hexane was introduced to the packing at the top of the column. Carotenes, as indicated by the orange band was eluated from the column by gravity with hexane. Two hundred milliliters of hexane eluate was collected from the bottom of the column and rotavaporized to give a carotene-rich fraction. Ethanol was then added to the column to eluate the remaining components of the concentrate from the column. One hundred milliliters of the eluate was collected and rotavaporized. The concentration of carotene of the first fraction (carotene-rich fraction) and the second fraction as determined by spectrophotometry in Example I and II was about 389,000 ppm and 6,700 ppm respectively. The vitamin E content of the second fraction as determined by HPLC in Example II and III was about 6,200 ppm. Yield of carotenes recovery was about 99%.

EXAMPLE VI

An open column having a length of one hundred millimeters and an internal diameter of thirty millimeters was wet packed with hexane and silica gel (10 gram, 70–230 mesh grade), as in Example II and III. A 0.50 gram sample of the 4% carotene concentrate obtained in the same manner as in Example I was dissloved in 5 milliliters of hexane was introduced to the packing at the top of the column. Carotenes, as indicated by the orange band was eluated from the column by gravity with hexane. Two hundred milliliters of hexane eluate was collected from the bottom of the column and rotavaporized to give a carotene-rich fraction. Methanol was then added to the column to eluate the remaining components of the concentrate from the column. One hundred milliliters of the eluate was collected and rotavaporized. The concentration of carotene of the first fraction (carotene-rich fraction) and the second fraction as determined by spectrophotometry in Example I and II was about 327,000 ppm and 9,100 ppm respectively. The vitamin E content of the second fraction as determined by HPLC in Example II and III was about 9,200 ppm. Yield of carotenes recovery was about 87%.

EXAMPLE VII

An open column having a length of one hundred millimeters and an internal diameter of thirty millimeters was wet packed with petroleum ether (bp. 40–60° C.) and silica gel (12 gram, 70–230 mesh grade), as in Example II and III. A 0.50 gram sample of the 4% carotene concentrate obtained in the same manner as in Example I was dissloved in 5 milliliters of petroleum ether was introduced to the packing at the top of the column. Carotenes, as indicated by the orange-red band was eluated from the column by gravity with petroleum ether. The first fraction of one hundred milliliters of petroleum ether eluated was collected, followed by a second fraction of two hundred milliliters of petroleum ether of eluated carotenes, as indicated by the orange band. The two fraction collected from the bottom of the column were rotavaporized to give two carotene-rich fractions. Ethanol was then added to the column to eluate the remaining components of the concentrate from the column. Sixty milliliters of the eluate was collected and rotavaporized to give a third fraction. The carotene concentration of the first, second (carotene-rich fraction) and third fraction as determined by spectrophotometry in Example I and II were about 2,613 ppm, 805,227 ppm and 7,754 ppm respectively. Yield of carotenes recovery was about 98%.

EXAMPLE VIII

An open column having a length of one hundred millimeters and an internal diameter of thirty millimeters was wet packed with heptane and silica gel (12 gram, 70–230 mesh grade), as in Example II and III. A 0.50 gram sample of the 4% carotene concentrate obtained in the same manner as in Example I was dissloved in 5 milliliters of heptane was introduced to the packing at the top of the column. Carotenes, as indicated by the orange-red band was eluated from the column by gravity with heptane. The first fraction of two hundred and fifty milliliters of heptane eluated was collected, followed by a second fraction of seven hundred milliliters of heptane of eluated carotenes, as indicated by the orange band. The two fraction collected from the bottom of the column were rotavaporized to give two carotene-rich fractions. Ethanol was then added to the column to eluate the remaining components of the concentrate from the column. One hundred milliliters of the eluate was collected and rotavaporized to give a third fraction. The carotene concentration of the first, second (carotene-rich fraction) and third fraction as determined by spectrophotometry in Example I and II were about 5,306 ppm, 229,208 ppm and 9,024 ppm respectively. Yield of carotenes recovery was about 99%.

EXAMPLE IX

An open column having a length of one hundred millimeters and an internal diameter of thirty millimeters was wet packed with hexane and silica gel (12 gram, 70–230 mesh grade), as in Example II and III. A 0.50 gram sample of the 4% carotene concentrate obtained in the same manner as in Example I was dissloved in 5 milliliters of hexane was introduced to the packing at the top of the column. Carotenes, as indicated by the orange-red band was eluated from the column by gravity with hexane. The first fraction of two hundred milliliters of hexane eluated was collected, followed by a second fraction of six hundred milliliters of hexane of eluated carotenes, as indicated by the orange band. The two fraction collected from the bottom of the column were rotavaporized to give two carotene-rich fractions. Ethanol was then added to the column to eluate the remaining components of the concentrate from the column. One hundred milliliters of the eluate was collected and rotavaporized to give a third fraction. The carotene concentration of the first, second (carotene-rich fraction) and third fraction as determined by spectrophotometry in Example I and II were about 5,567 ppm, 1,000,000 ppm and 9,024 ppm respectively. Yield of carotenes recovery was about 98%.

EXAMPLE X

An open column having a length of one hundred millimeters and an internal diameter of thirty millimeters was wet packed with hexane and silica gel (12 gram, 70–230 mesh grade), as in Example II and III. A 0.50 gram sample of the 0.8% carotene concentrate obtained in the same manner as in Example I was dissloved in 5 milliliters of hexane was introduced to the packing at the top of the column. Carotenes, as indicated by the orange-red band was eluated from the column by gravity with hexane. The first fraction of two hundred milliliters of hexane eluated was collected, followed by a second fraction of five hundred milliliters of hexane of eluated carotenes, as indicated by the orange band. The two fraction collected from the bottom of the column were rotavaporized to give two carotene-rich fractions. Ethanol was then added to the column to eluate the remaining components of the concentrate from the column. One hundred milliliters of the eluate was collected and rotavaporized to give a third fraction. The carotene concentration of the first, second (carotene-rich fraction) and third fraction as determined by spectrophotometry in Example I and II were about 96,933 ppm, 929,130 ppm and 1915 ppm respectively. Yield of carotenes recovery was about 86%.

EXAMPLE XI

An open column having a length of one hundred millimeters and an internal diameter of seventy millimeters was wet packed with petroleum ether (bp. 40–60° C.) and silica gel (120 gram, 70–230 mesh grade), as in Example II and III. A 6.0 gram sample of the 0.8% carotene concentrate obtained in the same manner as in Example I was dissloved in 20 milliliters of petroleum ether was introduced to the packing at the top of the column. Carotenes, as indicated by the orange-red band was eluated from the column by gravity with petroleum ether. The first fraction of five hundred milliliters of petroleum ether eluated was collected, followed by a second fraction of 2.7 liters of petroleum ether of eluated carotenes, as indicated by the orange band. The two fraction collected from the bottom of the column were rotavaporized to give two carotene-rich fractions. Ethanol was then added to the column to eluate the remaining components of the concentrate from the column. Five hundred milliliters of the eluate was collected and rotavaporized to give a third fraction. The carotene concentration of the first, second (carotene-rich fraction) and third fraction as determined by spectrophotometry in Example I and II were about 553 ppm, 627,006 ppm and 222 ppm respectively. Yield of carotenes recovery was about 99%.

Equivalents

Those skilled in the art will appreciate that the invention described herein is suspectible to variations and modifications other than those specifically described. It is to be understood that the invention includes all such variation and modifications.

The invention also includes all the steps, features, compositions and compounds referred to or indicated in the specification, individually or collectively, and any all combinations of any two or more of said steps or features.

What is claimed is:

1. A process for the recovery of carotenes from carotene-containing natural oils and fats, said process consisting essentially of the steps of:
    (a) alcoholic esterification of the carotene-containing oils and fats with a monohydric lower alkyl alcohol without destroying the carotenes;
    (b) molecular distillation of an alkyl ester phase containing alkyl esters of fatty acids, carotenes, tocopherols and tocotrienols recovered from step (a) to remove the alkyl esters to give a carotene-rich concentrate, wherein the molecular distillation is carried out under conditions including a pressure of less than 60 mTorr and a temperature of less than 180° C.;
    (c) adsorptively separating and concentrating the carotene-rich concentrate to give a carotene-rich fraction and a fraction rich in said tocopherols and tocotrienols by
        (i) admixing said carotene-rich concentrate with a non-polar solvent consisting of hexane, heptane, petroleum ether or a mixture of any two or more of said non-polar solvents in an amount sufficient to dilute the carotene-rich concentrate and to facilitate separation of the carotenes from said concentrate,
        (ii) introducing the admixture to a column having a length of 100 mm and an internal diameter of 30 mm which is wet-packed with said non-polar solvent and an adsorbent consisting of normal silica gel, and
        (iii) contacting said silica gel adsorbent with additional non-polar solvent in an amount sufficient to separate the carotenes from said carotene-rich concentrate and recover a carotene-rich fraction; and thereafter
        (iv) contacting said silica gel adsorbent with a solvent consisting of isopropanol, acetone, ethyl acetate or a mixture of any two or more of said polar solvents or a mixture of said polar solvent with said non-polar solvent in an amount sufficient to separate said tocopherols and said tocotrienols from said carotene-rich concentrate, and recover a fraction rich in tocopherols and tocotrienols.

2. A process as claimed in claim 1, wherein the adsorption and separation of the carotenes from the carotene-rich concentrate is carried out at a temperature in the range of between 0° C. to 80° C.

3. A process as claimed in claim 1, wherein the molecular distillation is carried out at a temperature in the range of 130° C. to 170° C.

4. A process as claimed in claim 2, wherein the molecular distillation is carried out at a temperature in the range of 130° C. to 170° C.

* * * * *